United States Patent [19]
Markelov

[11] Patent Number: 5,441,700
[45] Date of Patent: Aug. 15, 1995

[54] HEADSPACE AUTOSAMPLER APPARATUS

[76] Inventor: Michael Markelov, 7276 Greenfield, Chesterland, Ohio 44026

[21] Appl. No.: 72,822

[22] Filed: Jun. 7, 1993

[51] Int. Cl.⁶ ............................................. G01N 35/00
[52] U.S. Cl. ................................. 422/83; 73/864.21; 73/864.91; 422/63; 422/80
[58] Field of Search ........... 73/864.21, 864.23, 864.81, 73/864.82, 864.83, 864.84, 864.85, 864.86, 864.87, 864.91; 422/63, 80, 72, 83, 307; 436/157

[56] References Cited

U.S. PATENT DOCUMENTS

| | | |
|---|---|---|
| 3,151,073 | 9/1964 | Anthon ................... 422/72 |
| 3,945,796 | 3/1976 | Nagamatsu et al. ........... 422/307 |
| 4,080,175 | 3/1978 | Chulay et al. ............. 422/72 |
| 4,237,733 | 12/1980 | Kolb et al. ............. 73/423 A |
| 4,248,355 | 2/1981 | Kolb et al. ............. 422/102 |
| 4,476,733 | 10/1984 | Cholsta et al. ............. 73/863.91 |
| 4,478,095 | 10/1984 | Bradley et al. ............. 73/864.23 |
| 4,554,436 | 11/1985 | Cholsta et al. ............. 219/385 |
| 4,818,489 | 4/1989 | Gönner et al. ............. 73/864.82 |
| 5,110,743 | 5/1992 | Windisch et al. ............. 422/72 |
| 5,266,496 | 11/1993 | Dacruz ............. 436/157 |

Primary Examiner—James C. Housel
Assistant Examiner—Rachel Heather Freed
Attorney, Agent, or Firm—Ralph E. Jocke

[57] ABSTRACT

A headspace autosampling apparatus (92) for generating and delivering gaseous samples to a gas chromatograph or other instrument includes a plurality of vials (98) in a carousel (150). The vials are delivered one at a time from the carousel through a vial delivery mechanism (160) to a heated zone (146) wherein the substances (94, 96) to be analyzed reach equilibrium with the headspace (100, 102) above the samples in the vials, preferably using the full evaporation technique (FET). The vials are generally cylindrical and extend horizontally to facilitate attainment of equilibrium rapidly upon heating. The vials are also preferably rotated about their longitudinal axis prior to sampling so as to achieve a film effect on the interior walls of the vials which further aids in attainment of equilibrium. The apparatus is operative to first pressurize the headspace in the vial with an inert gas, and then to place said headspace in fluid communication with the inlet of a gas chromatograph wherein analytes in the headspace volume are analyzed to determine the composition thereof.

6 Claims, 6 Drawing Sheets

HEADSPACE AUTOSAMPLER APPARATUS

TECHNICAL FIELD

This invention relates to analysis of materials. Specifically, this invention relates to an FET headspace autosampler apparatus for generating and delivering gaseous samples to an analytical instrument such as a gas chromatograph.

BACKGROUND ART

Gas chromatography is an advantageous method for analyzing minute quantities of complex mixtures from biological and chemical sources. Gas chromatography may be used to determine the constituents in the mixture from which the sample is taken. Gas chromatography typically involves volatizing a sample to be analyzed and moving the sample in a stream of inert carrier gas.

The sample and carrier gas are delivered to a packing bed or column in the gas chromatograph. The different constituents in the sample move through the column at different rates. As a result, they are separated and appear one after the other at the output end of the column. At the outlet end the separated materials in the sample are identified through their properties of thermoconductivity, density differences or by ionization detectors, depending on the type of gas chromatograph.

Headspace sampling is a technique that involves testing a gaseous sample generated in a closed container above a solid or liquid substance to be analyzed. Sampling gaseous material avoids the introduction of nonvolatile or solid particles into the inlet of the gas chromatograph, which is not desirable.

Headspace sampling involves establishing an equilibrium in a sealed vial between the substance to be analyzed and the volume above the substance. Equilibrium is established by heating the sample in the vial. A gaseous sample is then taken from the headspace and delivered to the analytical instrument.

This technique has advantages because it assures that only gaseous material enters the gas chromatograph or other instrument. Further, because the sample is vapor, the amount of the sample may be much larger than a liquid sample. This increases the sensitivity of the analysis. These advantages of headspace sampling make it a useful technique in the analysis of polymers, latexes, paints, foods, biological materials, environmental samples, pharmaceuticals, fragrances and other substances.

Headspace sampling has certain limitations however. First, the volatility of a particular substance at a given temperature varies depending on the matrix of other materials it is mixed with. For example, the same concentration of benzene in water and in gasoline will have very different concentrations of benzene in the headspace at the same temperature. Therefore, in the prior art, it has been necessary to prepare calibration samples to simulate the matrix of materials in the substance being analyzed. However, this is impossible in cases of a solid sample or a substance that is completely unknown.

A further drawback of current headspace sampling techniques is that it takes many samples a long time to reach equilibrium between the condensed and vapor phases. Achieving equilibrium with current equipment often requires hours of heating. This is particularly true for viscous or solid substances. Some have tried agitation of the sample and vial in an attempt to shorten equilibrium times, but this has not proven effective and sometimes causes contamination problems.

Several approaches to headspace sampling have been used in the prior art. Each of these approaches suffers the drawback that removal of the gaseous sample from the headspace disturbs the equilibrium. Such disturbance of the equilibrium can cause poor repeatability. A further problem common to prior art techniques is that a disturbance in equilibrium may vary from sample to sample depending on the technique used and the properties of the materials being analyzed.

One approach to headspace sampling used in the prior art is syringe sampling. This technique involves removing a sample of gaseous material from the headspace over a substance to be analyzed, using a syringe. The disturbance of the equilibrium in the headspace using this technique depends on the amount of headspace in the sample vial compared to the volume of the sample. It also depends on the speed of removal of the sample, as removal of the material from the headspace will tend to cause more of the substance to enter the vapor phase to establish a new equilibrium.

A further problem with the syringe technique is that when the syringe is removed from the vial, some of the vapors will expand and escape to atmosphere prior to injection of the sample into the inlet port which carries the sample into the column of the gas chromatograph. Another drawback is that material in the sample may begin to condense due to cooling before the sample enters the gas chromatograph. As a result, not all the material in the sample may be delivered, which causes poor repeatability.

Another headspace sampling technique used in the prior art is explained with reference to FIG. 1. This approach is called fixed volume injection. The fixed volume system 10 has a sample vial 12 with a substance 14 therein. The vial is generally a cylindrical vial which is held in the upright position during sampling. This is standard with all prior art headspace sampling techniques.

A sampling needle 16 is positioned in the headspace in the interior volume of the vial above the substance. The needle is in fluid communication with a first port 20 of a six port valve 22. Six port valve 22 alternatively places first adjacent ports, shown connected by the solid lines in the drawing, in fluid communication when the valve is in a first condition. In a second condition of the valve, the alternative adjacent ports shown connected by the dashed lines are connected.

The second and fifth ports of the valve 24 and 26, respectively, are connected by a sample loop 27. The third port 28 is connected to the inlet of the gas chromatograph. The fourth port 30 is connected to a source of inert carrier gas such as helium. The sixth port 32 is connected to a valve 34 that is alternatively connected to a source of inert gas or to atmosphere.

In operation, with valve 22 in the condition shown in the drawing, the inert gas pressure of port 32 is applied to headspace 18 through port 20. In this condition of valve 22, the carrier gas passes through the sample loop 27 to the gas chromatograph inlet through ports 30, 26, 24 and 28.

The conditions of valves 22 and 34 are then changed. In these alternative conditions, the headspace sample is directed into the sample loop through connection of ports 20 and 24 of the valve. The sample loop 27 also vents to atmosphere due to the connection of ports 26 and 32 and the opening of valve 34. As a result, sample loop 27 is filled with gaseous material from the headspace of the vial.

The return of valve 22 to the first condition causes the carrier gas to wash the sample material in the sample loop into the inlet of the gas chromatograph. This is accomplished because the carrier gas is connected to port 26 and pushes the material in the sample loop through ports 24 and 28.

The operation of the system 10 includes several timed functions including the time of heating the sample to attempt to achieve equilibrium, pressurization time for the headspace, time of venting the headspace vapors through the sample loop and the time of washing the sample loop with the carrier gas. All of these timed event functions impact the results produced by the gas chromatograph. Particularly problematic is that venting the sample to atmosphere disturbs the headspace equilibrium. Also, it is a common problem that the headspace vapor passing through the lines and valves of the system, will begin to condense, which further adversely affects repeatability and cross contamination.

An alternative type of prior art headspace sampling system 36 is shown in FIG. 2. In this system, a vial 38 contains a substance 40 to be analyzed. The headspace 42 is pressurized with carrier gas through a sampling needle 44. At the same time as the headspace is pressurized, the column of the connected gas chromatograph 46 is pressurized to the same pressure. Carrier gas flow to the vial and to the gas chromatograph is then shut off. Thereafter the headspace 42 of the vial is the source of gas delivered to the gas chromatograph.

This type of sampling is suitable for use with gas chromatographs that have high column pressures. However, many gas chromatographs have low column pressures which make this prior art approach unsuitable. This is because at low pressures the amount of sample delivered into the column of the gas chromatograph is too small to produce accurate results.

In conclusion, prior art sampling devices have inherent problems due to the effects of condensation or loss of the constituents of the sample before entry into the gas chromatograph. Prior art systems also have the drawback that long heating times are required to insure that the headspace reaches equilibrium with the substance to be analyzed.

Thus there exists a need for a headspace autosampling apparatus that provides greater sensitivity and repeatability, reduces cycle times and is readily adaptable for use with a variety of substances and types of analytical instruments.

DISCLOSURE OF INVENTION

It is an object of the present invention to provide a headspace autosampling apparatus that provides high sensitivity with greater repeatability.

It is a further object of the present invention to provide a headspace autosampling apparatus that provides reduced cycle times and faster sample turnaround.

It is a further object of the present invention to provide a headspace autosampling apparatus that is capable of automatically handling a large number of samples.

It is a further object of the present invention to provide a headspace autosampling apparatus that is compact and which can be mounted directly on a gas chromatograph or other analytical instrument.

It is a further object of the present invention to provide a headspace autosampling apparatus that is suitable for use with a wide range of sample types.

It is a further object of the present invention to provide a headspace autosampling apparatus that is suitable for use with a variety of gas chromatography and other analytical units.

It is a further object of the present invention to provide a headspace autosampling apparatus that is adapted for use with full evaporation technique (FET) headspace analysis.

It is a further object of the present invention to provide a headspace autosampling apparatus that employs sample vials that are adapted for robotic handling.

It is a further object of the present invention to provide a headspace autosampling apparatus that includes a manual sample injection port that enables manual injection of samples without loss of sensitivity.

It is a further object of the present invention to provide a headspace autosampling apparatus that may be operated under flexible programmable control, that simplifies method development and enables optimization of headspace conditions.

It is a further object of the present invention to provide a headspace autosampling apparatus that provides for manual override of operations in the machine cycle.

It is a further object of the present invention to provide a headspace autosampling apparatus that is reliable and has simplified maintenance and diagnostic characteristics.

Further objects of the present invention will be made apparent in the following Best Modes for Carrying Out Invention and the appended claims.

The foregoing objects are accomplished in the preferred embodiment of the present invention by headspace autosampling apparatus that includes a plurality of vials for holding substances to be analyzed. The vials are generally cylindrical and are vertically stacked in groups with the longitudinal axis of the vials extending horizontally.

The vials are fed from a group one at a time into a heated zone inside the apparatus. Because of the large interface between the headspace volume in the vials, and the substances because of the vial orientation, equilibrium between the substance and the headspace is rapidly achieved. In addition, the vial is rotated about its longitudinal axis which causes a film of the substance to form on the wall of the vial above the substance. This further facilitates evaporization of the substance into the headspace and reduces the time necessary to achieve equilibrium.

The headspace is then pressurized in the apparatus through a pressurization line. The headspace volume is pressurized to a predetermined pressure or flow through a flow needle. The inert gas which is used to pressurize the headspace is carefully controlled in temperature and is maintained at the same temperature as the vials so as to not upset the equilibrium therein. Thereafter, the pressure in the headspace is relieved to the inlet of a gas chromatograph or other instrument, through valving and lines that are also carefully temperature controlled. Thereafter, the sample is washed into the inlet of the gas chromatograph using a carrier gas. The temperature of the carrier gas is also controlled to avoid condensation, and its path through the apparatus assures that all of the sample is analyzed.

The headspace autosampling apparatus of the present invention is adapted to run samples continuously and to accumulate data on a large number of samples without the need for reloading or reprogramming. The preferred embodiment of the invention includes several functional features to insure accuracy, safety and repeatability of the sampling process. The preferred embodiment of the invention is particularly adapted for headspace analysis using a new technique known as full evaporization technique (FET) which enables minimization of matrix effects.

BEST MODES FOR CARRYING OUT INVENTION

Figure 1:
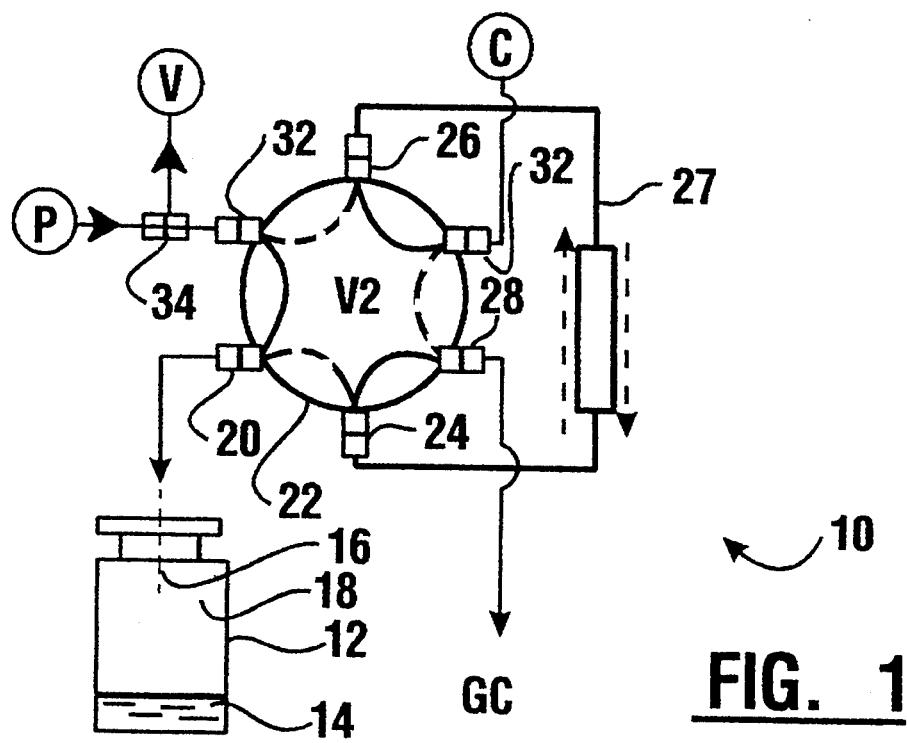
FIG. 1 is a schematic view of a fixed loop prior art headspace sampling system previously discussed.
Figure 2:
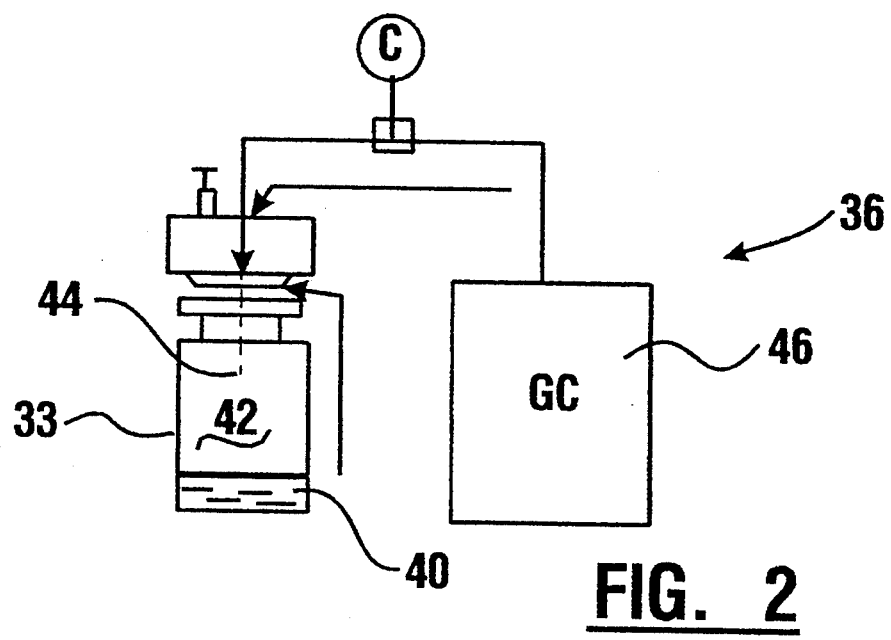
FIG. 2 is a schematic view of a balance pressure prior art headspace sampling system previously discussed.
Figure 3:
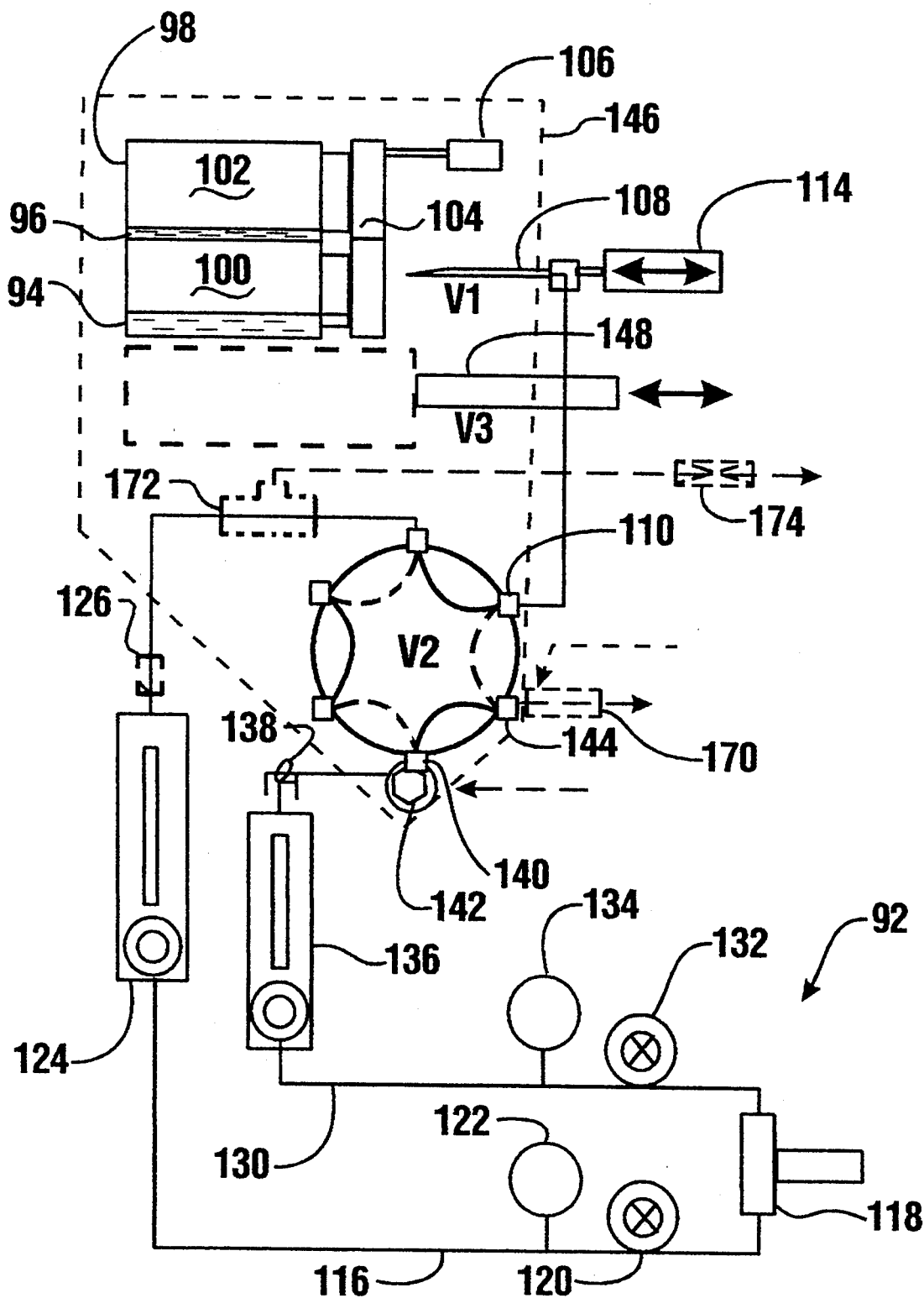
FIG. 3 is a schematic view of a headspace autosampling apparatus of a preferred embodiment of the present invention.

Referring now to the drawings and particularly to FIG. 3, there is shown therein a schematic view of the preferred embodiment of a headspace autosampling apparatus of the present invention, generally indicated 92. The apparatus is adapted for sampling substances 94, 96 located in identical vials 98. The vials are generally cylindrical and are positioned to have a horizontal dimension greater than a vertical dimension. Each vial 98 has an interior volume which defines a headspace 100, 102 above the substances therein 94, 96, respectively.

Figure 9:
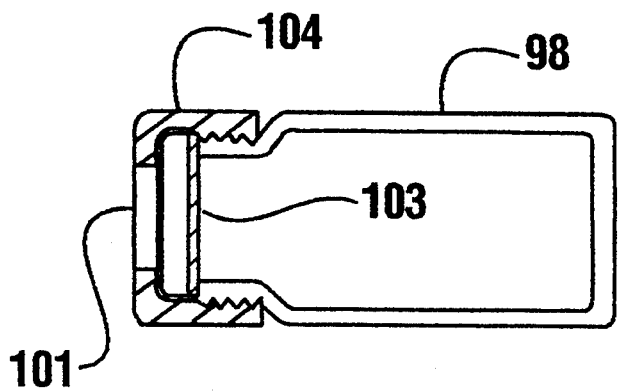
FIG. 9 is a cross sectional view of a sample vial used in the preferred embodiment of the invention.

Vials 98 include removable caps 104 at a first axial end of the vials (see FIG. 9). A silicone membrane 101 which serves as septum means extends across an opening in each cap. In the preferred embodiment the septum means includes a layer 103 of inert material at its interior surface. In the preferred embodiment the layer is 10–20 mils of Tetrafluoroethy-lene (TFE). The membrane is preferably 125 mils in thickness. The vial is preferably 2.5 inches long and 1.125 inches in outside diameter, with an internal volume of 25 milliliters.

Figure 7:
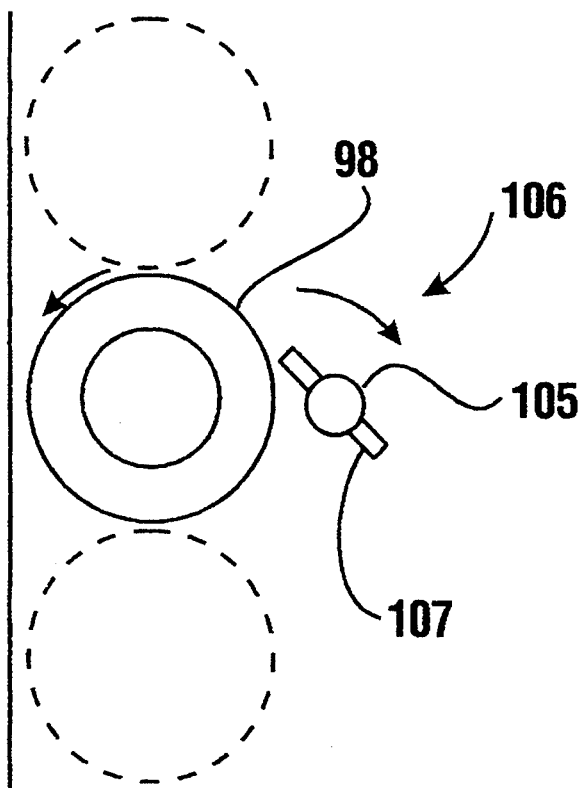
FIG. 7 is a side view of the sample vials in the passage of the headspace sampling apparatus, and the vial rotation mechanism.
Figure 8:
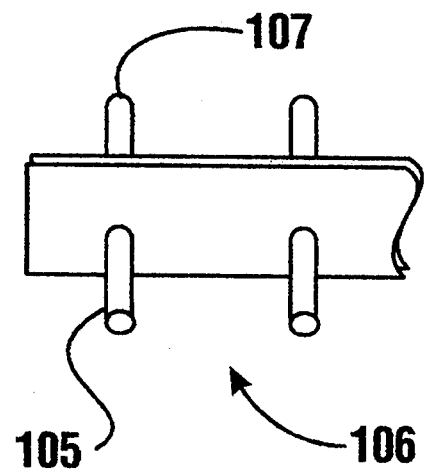
FIG. 8 is a right side view of the vial rotation mechanism shown in FIG. 7.

A motor driven rotating means 106 is adapted for rotating vials 98 about the longitudinal axis prior to sampling. As shown in FIGS. 7 and 8 rotating means 106 preferably includes a slowly rotating shaft 105. Shaft 105 has a plurality of radially extending flexible rubber rods 107 extending therefrom. The rods engage the cylindrical side of the vial during each rotation to rotate the adjacent vial as shown. However, the vials are enabled to move downward past rotating means 106.

In the apparatus as schematically shown in FIG. 3, a flow needle 108 is in fluid communication with a port 110 of a six port valve 112. Flow needle 108 is mounted in connection a horizontal actuator 114 such as a solenoid plunger. When actuator 114 moves inward toward the adjacent vial, the flow needle pierces the silicone membrane septum means 101 and is placed in fluid communication with the headspace 100. The flow needle 108 is somewhat above center of the longitudinal axis of the adjacent vial. This helps to assure that the flow needle is disposed vertically above the level of substance 94.

A pressurization line 116 is connected to a source 118 of inert gas which is preferably helium. Pressurization line 116 includes a regulator 120 and has a pressure gauge 122 thereon. Pressurization line 116 includes a first flow meter 124 as well as a pressure sensor 126 therein. Pressurization line 116 is connected to a port 128 of the six port valve 112. Flowmeter 124 in the preferred embodiment gives a visual as well as an electrical indication of the flow condition of the gas passing therethrough as hereinafter explained.

A carrier gas line 130 is also connected to the source 118 of inert gas. The carrier gas line includes a pressure regulator 132 and a pressure gauge 134 therein. Carrier gas line 130 includes a second flowmeter 136 and a pressure release valve 138. Carrier gas line 130 is connected to a port 140 of valve 112. Carrier gas line 130 also includes therein a manual injection port 142 adjacent to port 140 of the valve.

Valve 112 includes a port 144 which is in fluid communication with an inlet of a gas chromatograph. As shown schematically in FIG. 3, the vials 98, the flow needle 108, valve 112 and the pressurization and carrier lines 116 and 130 are all housed in a heated zone 146 in the apparatus 92. The elevated temperature of the heated zone 146 is maintained by electrical heating means. It should be understood that all the lines adapted for gas flow in the heated zone are maintained at elevated temperatures consistent with that of the headspace of the vials to be sampled. This assures that there is no condensation of any material from the sample in the lines and that the equilibrium condition in the vial is not upset during the sampling processes.

The apparatus further includes any ejection plunger 148. Ejection plunger 148 is movable to eject vials from the apparatus after the headspace therein is sampled. The ejection plunger is operated in the preferred embodiment by a solenoid actuator to eject the vials from the heated zone. After a vial is ejected, it may fall outward into a basket or other container. When the ejection plunger is retracted, the vials above it fall downward in a passage which holds the vials in the heated zone in vertical alignment as shown in FIG. 7. The passage assures that the vial previously sampled is in position for ejection while the vial positioned immediately above it in the passage is in position for sampling. This arrangement further provides that the vial immediately above the vial in position for sampling is rotated by rotating means 106.

Figure 5:
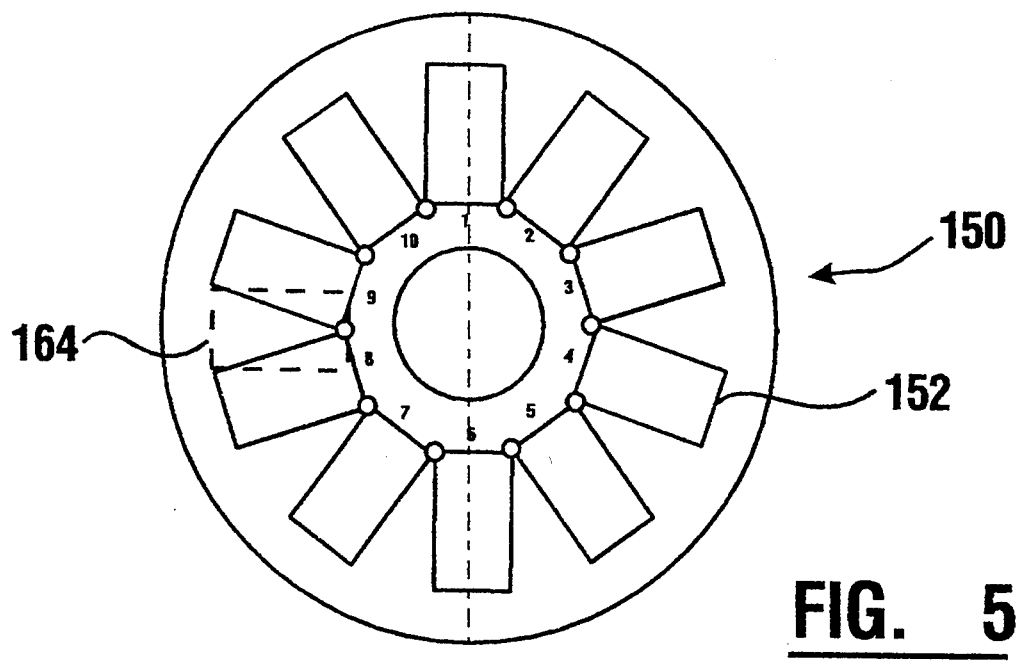
FIG. 5 is a top plan view of the carousel for holding sample vials of the preferred embodiment of the present invention.
Figure 6:
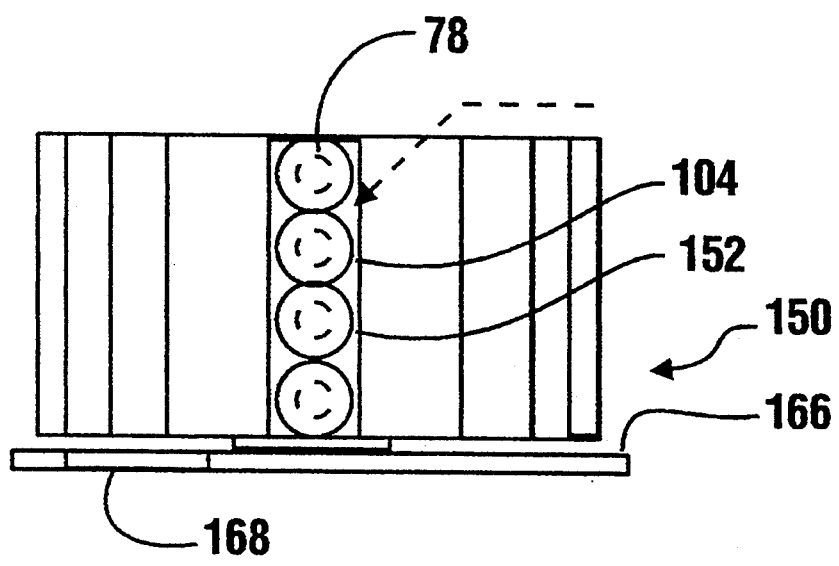
FIG. 6 is a right side view of the carousel shown in FIG. 5.

The headspace autosampling apparatus of the preferred embodiment of the present invention is adapted for sampling various substances in large numbers of vials and on a continuous basis. In the preferred embodiment, the apparatus includes a carousel 150 (see FIGS. 5 through 6) which serves as a holding means. Carousel 150 holds a plurality of vials 98 which are vertically arranged in groups 152. The carousel is adapted for holding 10 groups of four vials each in the preferred embodiment. When positioned in the carousel, the vials are all arranged so that their caps 104 and the rubber septum means therein are outwardly directed.

The carousel 150 is rotationally movable by an indexing means such as a stepper motor or other type of motor which is operable to rotate the carousel. The indexing means is operable to rotate the carousel into a desired position for feeding the vials 98 into the passage in the heated zone wherein they are heated, rotated and sampled. The carousel 150 is mounted above a housing 154 (see FIG. 4) which includes an oven enclosure 156. Oven enclosure 156 encloses heated zone 146. Oven enclosure 156 includes a lateral opening 158 through which vials ejected by ejection plunger 148 pass out of the device. The ejection plunger is sized similar to opening 158 and is generally extended during most of the machine cycle, except when it retracts to engage a vial for ejection. As a result the ejection plunger avoids heat loss through the opening to help maintain a constant temperature in the heated zone.

The housing 154 includes a vial delivery mechanism 160 thereon. Mechanism 160 includes a sliding member 162 which is positioned above the heated zone. The sliding member 162 includes an aperture 164 therein. The aperture is sized for accepting a single vial 98 so that the wall bounding the vial at the top is aligned with the top of the sliding member.

Figure 4:
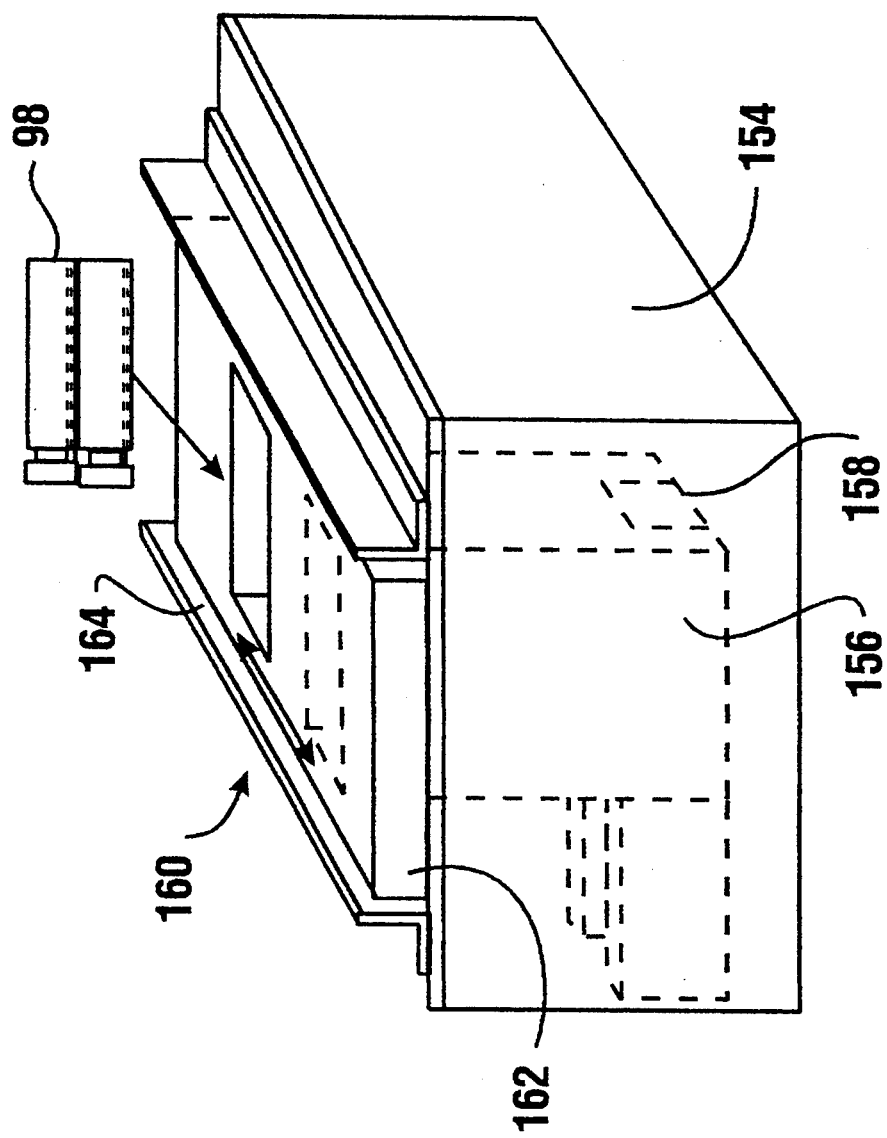
FIG. 4 is an isometric view of an oven portion and sample delivery mechanism of the preferred embodiment of the present invention.

The sliding member 162 is movable by a feed mechanism, which in the preferred embodiment includes a solenoid, between a first aperture position shown in FIG. 4 and a second aperture position which is shown in phantom. In the first aperture position, the aperture 164 is enabled to receive a vial from one of the groups 152 in the carousel. In a second position of the aperture, the aperture is positioned over the passage into which the vials pass into the heated zone for eventual sampling.

The sliding member 162 has a wall extending adjacent its underside so that a vial in the aperture moves in captured relation with the sliding member until the sliding member reaches the second position. In the second position the vial falls into the passage and enters the heated zone. In the second position the vial is in vertically stacked relation with other vials in the passage which are being heated and are awaiting sampling. The delivery mechanism 160 not only operates to deliver the vials one at a time for sampling, but also serves as a cover for the passage into the heated zone. As a result, the mechanism helps to maintain the heated zone at a stable temperature.

A sensor (not separately shown) is also positioned in the housing 154 adjacent the aperture in the first position. The sensor, which is preferably a photosensor, is adapted for sensing when no vials remain in a group. In this condition the control logic of the apparatus causes the carousel to rotate until the next group is over the aperture. The logic which controls the machine operates to continue rotation of the carousel until all the groups have been tried and it is determined that no additional vials are available for sampling, at which point the apparatus is shut off after the last vial in the passage is sampled.

It should be noted that carousel 150 includes a base plate 166. The base plate includes an opening 168 which corresponds to the first position of aperture 164 of the sliding member. The base plate 166 also operates to support vials 98 in the groups 152. As the carousel indexes, the bottom vials in the groups move rotationally about their longitudinal axis. This rotation also causes the vials above to rotate. This rotation during indexing aids in producing a film effect, which produces a film of the substance to be analyzed to remain on the interior walls of the vials as they rotate. The film effect facilitates the attainment of equilibrium in the headspace of the vial when the vial reaches the heated zone.

The headspace autosampling apparatus of the present invention is operated under the control of a programmable processor. The processor preferably includes several built in programs as well as the ability to be programmed with custom programs through an interface port. The control programs control the times for loading of the vial from the carousel 150 into the passage for heating. The programs also control the movement of the flow needle to pierce the septum means of the vial and the condition of the six port valve. The programs also typically control the ejection plunger which operates to eject a vial after sampling.

The preferred form of the invention also includes other features in the control program to assure safe operation and to facilitate the interface of the apparatus with a gas chromatograph or other analytical instrument. These features include temperature sensors in the heated zone 146 to insure that the unit will not operate to produce samples if the temperature in the heated zone is not within certain limits. In the preferred embodiment the heated zone is designed to operate in the range from 60 to 200 degrees Celsius. In the event the temperature of the oven should exceed a programmable limit, the controller of the unit executes a built-in alarm program routine. This routine operates to eject all sample vials from the heated zone, and then shuts off the device. This avoids possible dangerous conditions from overheating. The apparatus also includes an interface with a gas chromatograph or other instrument which can be used to insure that the instrument is operating properly and is ready to receive samples before the autosampling unit commences operation.

Other novel control aspects of the invention include a feature which allows relief of the pressure on the column of the gas chromatograph by opening a pressure release valve 138 and closing it again prior to delivering a sample. Such relief of the column pressure is desirable where the column pressure is high and may resist the infiltration of sample material, or in situations where high pressure may adversely impact sensitivity. The pressure release valve can also be used to relieve pressure in the vials after sampling, in which case its outlet may be ducted to a suitable trap. Further control functions are associated with the use of a trap shown in phantom as 170 on the line leading to the inlet of the gas chromatograph which may be used for trapping and/or later delivery of constituents in the samples. Further features of the control logic provide for counting and identifying samples and for shutting off the gas chromatograph when all the samples have been sampled. The control logic also is operative to detect fault conditions and to shut off the apparatus when fault conditions are detected.

The preferred form of the invention provides flexibility by enabling programmed control of all the functions, as well as hard wired control through externally mounted electrical terminal strips. This enables simplification of method development and optimization of headspace conditions. The preferred form of the apparatus of the present invention also includes manual override controls for the functions performed by the unit.

In operation, the headspace autosampling apparatus of the present invention operates to deliver gaseous samples to an inlet of a gas chromatograph or other analytical instrument in the ways hereinafter described. The apparatus is first allowed to heat up to the desired operating temperature of the heated zone. Once the unit is at operating temperature, and is loaded with a plurality of vials 98 holding any calibration samples and the material to be analyzed, the unit is ready to begin operation.

The carousel 150 and the vial delivery mechanism 160 is operated to begin delivering vials 98 into the heated zone 148 by transferring them into the passage. In the passage the vials 98 are in vertically aligned relation. Once in the heated zone the headspace volumes in the vials quickly reach equilibrium. The achievement of equilibrium is facilitated not only by the rotation of the vials which is caused by the movement of the carousel, but also by rotation of the vials in the passage by rotating means 106. Once a vial in the passage is adjacent with flow needle 108, the actuator 114 moves the flow needle forward to pierce the septum means bounding the headspace of the vial.

The six port valve 112 is initially in position to deliver pressurization flow of inert gas into the headspace 100 of the vial being sampled. This flow is continued until the pressurization flow observed by the operator at flow meter 124, or preferably as electrically sensed, reaches zero. Once the vial is fully pressurized, six port valve 112 changes its condition so that the headspace 100 is in fluid connection with the inlet of the gas chromatograph through port 114. Thereafter, valve 112 returns to its first condition as shown in FIG. 3 so that the carrier gas is delivered through the flow conduit in the six port valve that was previously connected to the headspace. As a result, the sample, including the material in the flow conduit in the six port valve, is washed into the inlet of the gas chromatograph.

Once the sample is taken, the flow needle withdraws from the vial and the ejection plunger 148 retracts from the position shown in FIG. 3. This enables the vial 98 at the sample position to fall downward. The ejection plunger then moves forward to eject the vial from the machine through opening 158. At the same time, the vial immediately above in the passage is ready for sampling. The process is repeated as the delivery mechanism continues to deliver additional vials into the passage for sampling.

An advantage of the preferred embodiment of the present invention is that in the gas injection mode, if the gas flow at flow meter 124 does not reach zero, it is known that there is a leak and the results will be unreliable. Likewise, if the flow at flow meter 136 should fall to zero during the time that it is operable to wash the sample into the inlet of the gas chromatograph, it is known that there is a problem. These conditions may be signalled by use of an alarm or may be recorded by the computer and correlated with the particular sample vial, so that the results are questioned.

In certain environments where the column pressure of a gas chromatograph is high, the operating cycle of the apparatus of the present invention may include the opening of pressure release valve 138 prior to delivery of a sample to the gas chromatograph. The opening of the pressure release valve 138 will relieve the pressure on the column and will enable the sample to flow into the inlet of the gas chromatograph at lower pressures.

The flow meter 136 also enables setting the flow so that the sample is delivered for analysis at the desired speed.

An alternative mode of operation for the preferred embodiment of the headspace autosampling apparatus is to control the pressurization of the headspace in accordance with pressure sensed at sensor 126. The pressurization of the vials to a uniform pressure rather than to a zero flow condition has the advantage of reducing the affects of the volatility of the materials in the sample matrix. Such approach also avoids conditions of too short pressurization time which may cause inadequate volume samples, or too long pressurization time which may result in diffusion of the vapor out of the headspace.

The method of control of the apparatus by pressurization of the headspace to a uniform pressure also enables identification of fault conditions. This is because a problem is immediately detected if the desired pressure is not achieved. As a result, it is known that any sample produced from the headspace of the corresponding vial is not meaningful data and should be disregarded.

The invention is also enabled to conduct multiple headspace extraction analysis by modifying the operating cycle of the apparatus. In multiple headspace analysis the headspace volume of the same sample is sampled by repeated withdrawal of material. By extrapolating from the decreasing concentration of the substance of interest, the original concentration of the material may be estimated. The repeated withdrawal of material from the headspace volume of a sample is accomplished by valve 172 and trap 174 shown in FIG. 3, operating the apparatus under control of a control program for this procedure in the processor.

The invention is preferably operated in accordance with the analytical method known as the full evaporation technique (FET). Using FET headspace analysis matrix effects in samples are reduced. FET involves reducing the sample size and correspondingly increasing temperatures so that analytes are transferred nearly completely from a condensed matrix to a confined vapor phase. This effectively eliminates the effect of the partition coefficient for the matrix. The technique is described in detail in the recent paper entitled "*Matrix Independent Headspace Gas Chromatographic Analysis-The Full Evaporation Technique*". Analytica Chimica Alta, 276 (1993) 235-245, Elsevier Science Publishers B.V., Amsterdam, authored by Dr. Michael Markelov and John P. Guzowski, Jr.

The preferred embodiment of the present invention is particularly well adapted for operation using FET autosampling. The use of the horizontally oriented sample vials as well as the film effect achieved by rotation of the vials about their longitudinal axis prior to sampling is particularly advantageous in achieving near complete vaporation of the substances of interest. Further, the careful temperature control of the pressurization gas and the sample assure reliable delivery of the sample.

Figure 10:
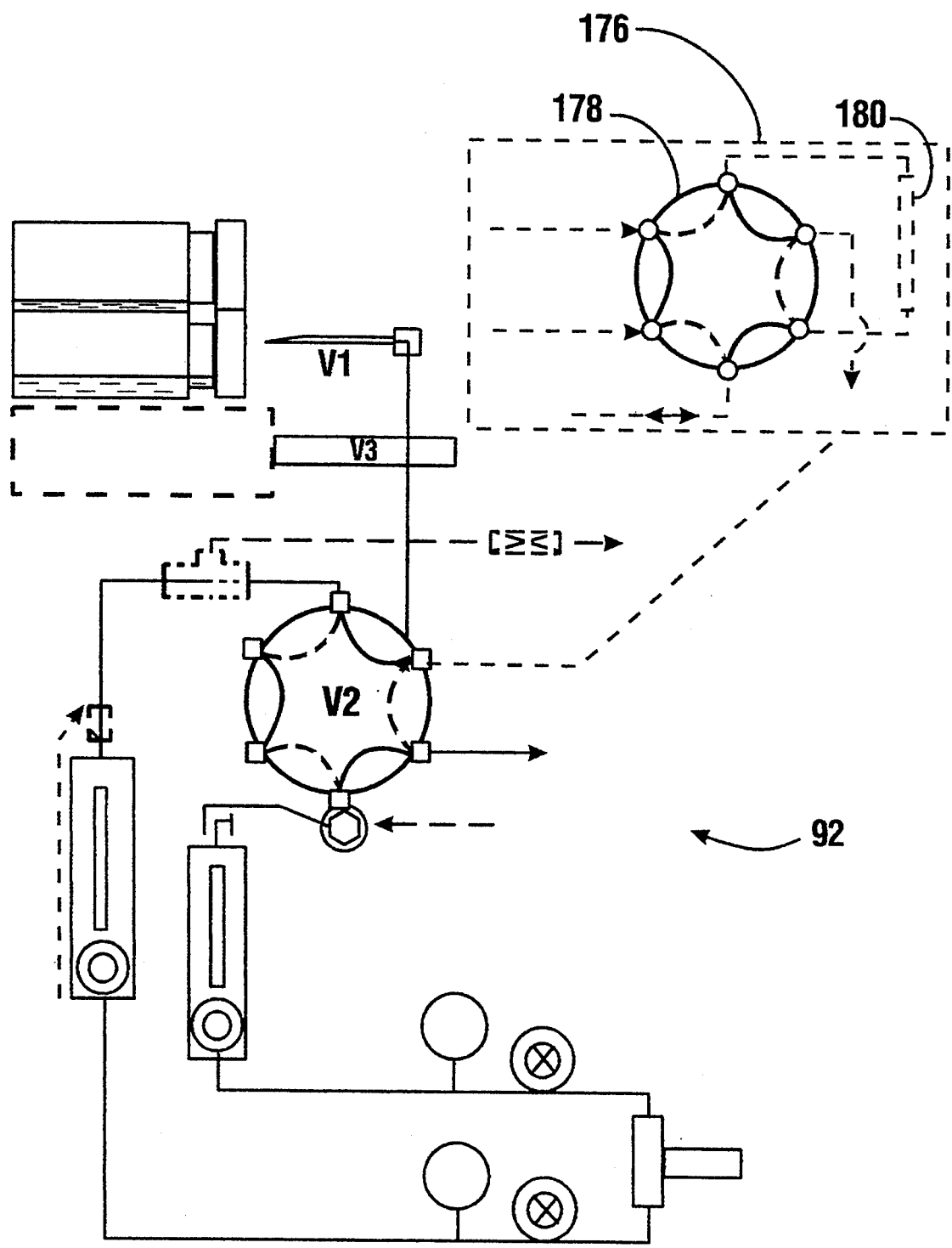
FIG. 10 is a Schematic view of an alternative plumbing arrangement of the headspace sampling apparatus which includes a trap.

The apparatus 92 may alternatively be operated to employ a trap option as shown in FIG. 10 by the alternative connection arrangement 176 for the six port valve 178. In this alternative arrangement, a sample vial is pressurized in the manner previously described while carrier gas flows through a trap 180 to the gas chromatograph as shown in the valve position of FIG. 10.

When the condition of the six port valve 178 changes from that shown in FIG. 10, the sample passes through trap 180, and the material which is not captured in the trap passes to the gas chromatograph. Thereafter, the valve condition is returned to that shown in FIG. 10, and the material in the trap is selectively delivered for analysis, such as through heating of the trap.

The apparatus of the present invention is readily adapted to the alternative arrangement 176 from the standard arrangement. This gives the instrument of the invention enhanced flexibility and greater value.

Although the preferred embodiment of the present invention employs a carousel for holding sample vials, other embodiments of the invention may employ other types of holding means. For example, the invention may be operated with a magazine type tower for holding a single stack of sample vials. Other embodiments may use other types of bins or feeding mechanisms.

A further advantage of the present invention is that it is very compact and may be mounted directly on a gas chromatograph or other analytical instrument. This avoids the need for long transfer lines and the possible inaccuracies which may result due to condensation in such lines.

The preferred embodiment of the invention is also equipped with a manual injection port. This port is particularly advantageous in that it is mounted on the six port valve, and manually injected samples travel by the same route as those taken automatically. As a result, the present invention may be operated by direct syringe sampling techniques without disconnecting the apparatus from the gas chromatograph, and the sensitivity is maintained for both sample types.

The headspace autosampling apparatus of the present invention achieves several fundamental advantages over the prior art as a result of sampling the headspace in cylindrical vials that are oriented so that their longitudinal axes extend in a generally horizontal direction. In this orientation, the surface area of evaporation for the substance to be analyzed is substantially increased from normal vials which are sampled with a longitudinal axis in the upright condition. The increase in surface area significantly decreases the time required to reach equilibrium between the substance and the headspace.

A further advantage of the orientation and configuration of the vials of the preferred embodiment of the headspace sampling apparatus of the present invention is that the thickness of the liquid layer of a substance to be analyzed is reduced. This reduction in thickness results in a dramatic increase in evaporation rate because diffusion time is a square function of the thickness of the substance layer. The horizontal position of the vials also enables their rotation while in the heated zone. As a result of rotation, liquid samples form a thin film on the interior walls of the vials. This greater surface area and decreased thickness of the film further reduce the time for the substance to achieve equilibrium with the headspace. Applicant has found that cylindrical vials in which the length is 1.6 times the radius are well suited for this purpose. However, other embodiments may use vials having other configurations.

The horizontal orientation of the sample vials also enables the preferred embodiment of the present invention to be much more compact and to hold a large number of samples in a machine that occupies very little space.

A further significant advantage of the present invention is that the vials include a novel twist off cap and septum construction. Prior art vials have all used a cover that is crimped over the vertically oriented opening. Crimping is undesirable because it makes reopening and reclosing vials difficult. This can be a problem where it is desired to add materials to the vial after initial closure.

A further fundamental advantage of the vials that are a part of the present invention is that they are well suited for handling by robots. This reduces labor costs and facilitates sample preparation of materials that pose risks in manual handling.

The preferred form of the vials of the invention achieve the desired results by using temperature resistant caps comprised of phenolic plastic and a silicone rubber septum means for sealing between the vial and the cap. The septum means is generally Tetrafluoro-ethy-lene (TFE) coated on its interior surface, but other coatings such as metallic coatings may be used depending on the type of sample.

Thus, the new headspace autosampling apparatus of the present invention achieves the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are for descriptive purposes and are intended to broadly construed. Moreover, the descriptions and illustrations are by way of examples and the invention is not limited to the details shown and described.

Having described the features, discoveries and principles of the invention, the manner in which it is constructed and operated, and the advantages an useful results attained; the new and useful structures, devices, elements, arrangements, parts, combinations, systems, equipment, operations and relationships are set forth in the appended claims.

I claim:

1. A headspace autosampling apparatus for generating and delivering gaseous samples from headspaces in vials holding substances for analysis to an inlet of an analytical instrument for analysis, comprising:

a plurality of generally cylindrical vials having an interior area which contains a substance therein, at least a portion of which is liquid and including a headspace above said substance;

means for rotating said vials about an axis extending longitudinally through said interior area and wherein said axis extends generally horizontally such that a film of said substance coats an interior surface of the vials whereby the rate of diffusion of the substance into the headspace is increased;

holding means for holding the plurality of vials, wherein said holding means holds said vials in a vertically stacked relation and with the longitudinal axis of each vial extending in a generally horizontal direction;

heating means for heating a heated zone;

means for delivering said vials one at a time from said holding means to the heated zone; and, means for placing the headspace of the vials in said heated zone in fluid communication with said inlet.

2. The apparatus according to claim 1 wherein said delivering means comprises a movable member means disposed vertically above said heated zone, said movable member means adapted for movement in a generally horizontal direction between a first position and a second position, said movable member means including an aperture means therein adapted for accepting a single vial in said aperture means, said aperture means positioned vertically below said holding means in the first position, whereby a vial is accepted therein, said aperture means in communication with a passage in the second position of said movable member means, said passage delivering said vial into said heated zone.

3. The apparatus according to claim 2 and further comprising ejection means for ejecting said vials from said heated zone one at a time after the headspace thereof has been placed in communication with said inlet of said instrument, and wherein upon ejection of a vial said further vials in said passage are enabled to move downward therein.

4. The apparatus according to claim 3 wherein said holding means comprises a carousel means for holding a plurality of groups of vertically stacked vials, and indexing means for rotating said carousel means and for placing said groups in vertically aligned relation with said first position of said aperture means of said movable member means.

5. The apparatus according to claim 1 and further comprising means for rotating said vials prior to delivery of said vial means to said sampling location.

6. The apparatus according to claim 1 wherein said vial include a threaded cap for closing said vials, said cap including an opening therein, said septum means accessible through said opening.

* * * * *